United States Patent [19]

Eisele et al.

[11] Patent Number: 5,342,645

[45] Date of Patent: Aug. 30, 1994

[54] METAL COMPLEX/CYANOACRYLATE COMPOSITIONS USEFUL IN LATENT FINGERPRINT DEVELOPMENT

[75] Inventors: John F. Eisele, Lakeland; Terrance P. Smith, Woodbury; Michael C. Palazzotto, St. Paul, all of Minn.

[73] Assignee: Minnesota Mining and Manufacturing Company, St. Paul, Minn.

[21] Appl. No.: 121,699

[22] Filed: Sep. 15, 1993

[51] Int. Cl.$^5$ .............................................. A61B 5/117
[52] U.S. Cl. ................................... 42.7/1; 106/19 R; 106/20 C; 118/31.5; 252/374; 427/145
[58] Field of Search ................... 427/1, 145; 118/31.5; 252/374; 106/19, 20

[56] References Cited

U.S. PATENT DOCUMENTS

| | | | |
|---|---|---|---|
| 3,322,680 | 5/1967 | Hedberg et al. | 252/301.2 |
| 4,504,408 | 3/1985 | Morton | 252/301.16 |
| 4,556,579 | 12/1985 | Lowell | 427/1 |
| 4,613,515 | 9/1986 | Reggio | 427/1 |
| 4,708,882 | 11/1987 | Asano et al. | 427/1 |
| 4,751,020 | 6/1988 | Marten et al. | 252/301.21 |
| 4,866,025 | 9/1989 | Byers et al. | 503/227 |
| 4,882,195 | 11/1989 | Butland | 427/1 |

FOREIGN PATENT DOCUMENTS

WO88/01616  3/1988  PCT Int'l Appl. .

OTHER PUBLICATIONS

"Two Simple Staining Procedures Which Improve the Contrast and Ridge Detail of Fingerprints Developed with 'Super Glue'(Cyanoacrylate Ester", by Kobus et al., Forensic Science Research Unit, Chemistry Department, Australian National University , Canberra (Australia), 1983. (no mo.).

"The Use of 1,8–Diazafluoren-9-one (DFO) for the Fluorescent Detection of Latent Fingerprints on Paper. A Preliminary Evaluation", by Pounds et al., Journal of Forensic Sciences, JFSCA, vol. 35, No. 1, Jan. 1990.

"Laser Detection of Latent Fingerprints: Difficult Surfaces", by Burt et al., Journal of Forensic Sciences, JFSCA, vol. 13, No. 2, Apr. 1985, pp. 364–370.

"Laser Detection of Latent Fingerprints: Treatment with Glue Containing Cyanoacrylate Ester", by Menzel et al., Journal of Forensic Sciences, JFSCA, vol. 28, No. 2, Apr. 1983, pp. 307–317.

"Laser Detection of Latent Fingerprints on Skin", by Menzel, Journal of Forensic Sciences, JFSCA, vol. 27, No. 4, Oct. 1982, pp. 918–922.

"Nitro–Benzofurazanyl Ethers–A New Series of Fluorigenic Fingerprint Feagents", by Almog et al., Journal of Forensic Sciences, JFSCA, vol. 32, No. 3, May 1987, pp. 585–596.

"Chemical Reagents for the Devleopment of Latent Fingerprints. III: Visualization of Latent Fingerprints by Fluorescent Reag3ents in Vapor Phase", by Almog et al., Journal of Forensic Sciences, JFSCA, vol. 25, No. 2, Apr. 1980, pp. 408–410.

"Applications of Laser Technology in Latent Fingerprint Enhancement", by Menzel, Journal of Forensic Sciences, pp. 136–162. (no date).

"Fingerprint Development by Ninhydrin and its Analogues", by Almog, Journal of Forensic Sciences, pp. 104–133. (no date).

(List continued on next page.)

*Primary Examiner*—Janyce Bell
*Attorney, Agent, or Firm*—Gary L. Griswold; Walter N. Kirn; Thomas C. Lagaly

[57] ABSTRACT

A cartridge useful in detecting fingerprints includes a housing with a chamber therein and an outlet from the chamber. The chamber contains a thermally stable porous or fibrous support impregnated with both:
1) a cyanoacrylate ester, and
2) a volatile, emissive lanthanide metal-complex or actinide metal-complex. Upon the application of sufficient heat to the support, the cyanoacrylate and metal complex volatilize and co-deposit on fingerprint residue to enhance the visualization of the fingerprint.

29 Claims, No Drawings

OTHER PUBLICATIONS

"Method of Latent Fingerprint Development", by Lee et al., Journal of Forensic Sciences, pp. 60–101. (no date).

"Absorption and Emission Spectroscopic Investigation of Cyanovinyldiethylaniline Dye Vapors", by Deshpande et al., Chemical Physics 142 (1990) 123–131. (no mo.).

"Contrast Enhancement of Cyanoacrylate-Developed Latent Fingerprints Using Biological Stains and Commercial Fabric Dyes", by Kempton et al., Journal of Forensic Sciences, JFSCA, vol. 37, No. 1, Jan. 1992, pp. 99–105.

"Inherent Fingerprint Luminescence-Detection by Laser", by Dalrymple et al., Journal of Forensic Sciences, vol. 22, No. 1, Jan. 1977 pp. 106–115.

"Comparison of Argon-Ion, Copper-Vapor, and Frequency-Doubled Neodymium: Yttrium Aluminum Garnet (ND:YAG) Lasers for Latent Fingerprint Development", by Menzel, Journal of Forensic Sciences, JFSCA, vol. 30, No. 2, Apr. 1985, pp. 383–397.

"Spectroscopic investigation of cyanovinyl-diethylaniline dyes in solutions", by Deshpande et al., Chemical Physics 148 (199) 141–154. (no date).

METAL COMPLEX/CYANOACRYLATE COMPOSITIONS USEFUL IN LATENT FINGERPRINT DEVELOPMENT

BACKGROUND OF THE INVENTION

1. Field of the Invention

The present invention relates to a system for fuming an object suspected of containing latent fingerprints thereon with cyanoacrylate vapors and an emissive metal complex. More particularly, the invention relates to developing a latent fingerprint by heating a cartridge which contains both of the following elements on a heat resistant support: 1) a polycyanoacrylate, and 2) a volatile, emissive lanthanide metal-complex or actinide metal-complex. Application of heat to the cartridge results in the production of emissive cyanoacrylate vapors. This invention also pertains to the use of a class of volatile, emissive metal-complexes that are particularly useful in the enhancement and visualization of latent fingerprints.

2. Background of the Art

Various methods have been described for the enhancement and subsequent visualization of fingerprints. Many of these techniques are discussed in chapters 3, 4, and 5 of Henry C. Lee and R. E. Gaensslen *Advances in Fingerprint Technology*, Elsevier, New York, 1991. One of the best methods for developing latent prints is to expose the article, suspected of containing the prints, to cyanoacrylate vapors. The vapors are preferentially deposited onto the fingerprint residue. It is generally believed that various components in the fingerprint residue cause the cyanoacrylate to undergo a polymerization reaction whereby an enhanced fingerprint image results.

U.S. Pat. No. 4,504,408 entitled "Fluorescent Vapor Fumes For Use With A Self-Contained Fingerprinting Kit" and U.S. Pat. No. 4,613,515 entitled "Fingerprint Development Kit and Process" describe methods of enhancing and visualizing fingerprints. In U.S. Pat. No. 4,504,408, fluorescent cyanoacrylate vapors are generated by allowing a liquid monomeric cyanoacrylate to contact an activator pad previously impregnated with a fluorescent compound and a composition which contains two components A and B. A is a mixture of chloroethane and methanol and B contains a polymerization catalyst in a mixture of the following solvents: nitromethane and/or nitroethane, methanol, toluene. An alternative construction involved adding the cyanoacrylate and the fluorescent dye to a gauze pad which had been treated with the two component composition A and B referred to above. Both these processes involve the transfer of liquid(s) and the release of several volatile organic compounds, in addition to producing the desired fluorescent cyanoacrylate fumes. As a result, that kit requires that the process be carried out in an enclosed area or preferably in an enclosed chamber. Also, once the liquid cyanoacrylate has been added, vapors are generated until the reaction has run its course, presumably when one of the reagents (i.e., the monomeric cyanoacrylate or the catalyst) is either consumed or otherwise neutralized, or when the heat generated is unable to sustain the production of the fluorescent cyanoacrylate vapors. No simple means of terminating the process once it has been started is given in this patent. In U.S. Pat. No. 4,613,515 a kit is also described. This kit is comprised of the following: 1) a container of a liquid cyanoacrylate monomer or polymer precursor and a polymerization inhibitor, 2) a separate container containing an inert pad having sorbed therewith at least one catalyst for the polymerization of a monomeric cyanoacrylate ester or polymer precursor, and a fingerprint development enhancer. The preferred pad material is either cotton or flax. Upon addition of the cyanoacrylate monomer to the pad, a reaction ensues, producing cyanoacrylate vapors and in some constructions fluorescent vapors. The pad is intended for a one time use. As in the previous kit, the reaction, once initiated, is allowed to proceed until either one of the reagents is exhausted or the heat generated by the reaction is insufficient to generate fluorescent cyanoacrylate vapors.

Other systems utilizing cyanoacrylate vapors have also been disclosed. WO 8801616-A teaches the use of solid Dieis-Alder adducts of cyanoacrylate as monomeric cyanoacrylate precursors. When these adducts are heated, the adducts undergo a retro-Diels-Alder reaction whereby monomeric cyanoacrylate derivatives are generated. Some of the cyanoacrylate derivatives have covalently attached fluorescent dyes. This system has the advantage of using a solid composition. However, the high molecular weight of some of the compositions and the resultant low vapor pressure of these fluorescent cyanoacrylate monomers limit the effectiveness of this approach. Other shortcomings of this system are discussed in a dissertation entitled "Detection Of Latent Fingerprints With Cyanoacrylates: New Techniques Involving Coloured And Photoluminescent Compounds" by Siaw-Jan Yong, The Australian National University, GPO Box 4, Canberra, ACT 2601 on pages 64–81. The above dissertation also discusses a device and a method for the volatilization of polycyanoacrylates. This apparatus consists of a glass chamber equipped with a controllable electric heating element attached to a heat conducting holder. The article suspected of having a fingerprint is suspended in the chamber by a wire. The heat conducting holder is charged with monomeric or polymeric cyanoacrylate and the heating element turned on. This device provides an excellent means of controlling the rate of vaporization. However, for field work it is somewhat cumbersome and requires an electric power source. A modified apparatus for the co-volatilization of cyanoacrylates and fluorescent compounds is also described. This apparatus is similar to the one previously described but contains a second, separate heating element. The co-volatilization experiments were accomplished by placing the cyanoacrylate on one holder and the fluorescent compound on the other holder, and then heating the two holders to separate temperatures to provide vapors of both species.

Other methods for visualizing fingerprints involve staining or dusting cyanoacrylate developed prints with a fluorescent dye or pigment or, alternatively, exposing cyanoacrylate developed prints to fluorescent dye vapors. These methods are discussed in the following references: J. Almog and A. Gabay, *Journal of Forensic Science*, 25, 1980, 408–409; J. Almog et. al., *Journal of Forensic Science*, 32, 1987, 585–596; E. R. Menzel, *Journal of Forensic Science*, 27, 1982, 918–922. E. R. Menzel et. al., *Journal of Forensic Science*, 28, 1983, 307–317; J. A. Butt and E. R. Menzel, Journal of Forensic Science, 30, 1988, 364–370; C. A. Pounds and R. R. Grigg, *Journal of Forensic Science*, 35, 1980, 169–175; H. K. Korbus, R. N. Warrener, and M. Stoilovic, Forensic Science Internation, 23, 1983, 233–240.

Post-treatment of cyanoacrylate fingerprints by pigments or stains has been disclosed in the following patents or patent applications: Japanese Patents: J02268744A and J6316194OA; U.S. Pat. Nos. 4,917,987, 4,794,260, and 4,708,882.

Various acrylate constructions containing fluorescent agents have been described. U.S. Pat. No. 3,322,680 relates to polymeric compositions containing a bis(benzoxazolyl) fluorescent agent. These compositions can be in the form of films, fibers, filaments, sheets, and other shaped objects. Although there are no specific references to cyanoacrylates, acrylates generally are described. U.S. Pat. No. 4,751,020 discloses UV-fluorescent cyanoacrylate adhesive compositions. The fluorescent agent is selected from either specific bis(benzoxazolyl) derivatives or specific coumarin derivatives. The composition may contain standard additives, such as polymerization inhibitors, thickeners, plastizers, perfumes, dyes, pigments, and polymerization catalysts.

In a copending patent application, U.S. Ser. No. 08/059,063, filed May 11, 1993 and bearing attorney's Docket No. FN 49571USA8A, several classes of organic compounds are identified which, when covolatilized with monomeric or polymeric cyanoacrylates, are useful in the enhancement of latent fingerprints. In general, these materials have molecular weights in the range of 100 to 500 Daltons and have fluorescent quantum yields greater than $10^{-4}$.

SUMMARY OF THE INVENTION

Co-volatilization, by the application of heat, of an intimate mixture of a volatile, emissive metal complex and either a monomeric cyanoacrylate ester or, preferably, a polymeric cyanoacrylate ester on an inert, thermally resistant substrate produces a chemical vapor that can be used to develop latent fingerprints. A preferred form of the invention is a volatile, emissive metal complex, a polymeric cyanoacrylate ester, and an inert fibrous (or porous) substrate contained in a cartridge which can be attached to a heating device. A preferred heating device is a butane-powered torch. Another aspect of the present invention has been the discovery of a class of emissive metal complexes that can be used in the above system. Yet another aspect of the invention is the discovery that lanthanide and actinide metal complexes with $\beta$-diketonate ligands are especially selective, in terms of co-depositing with the cyanoacrylate vapors on the fingerprinted residue. This results in excellent contrast between the fingerprinted residue and the background areas. Various europium $\beta$-diketonate complexes have been found to be particularly useful materials.

The present invention also provides a method for developing a latent fingerprint, comprising the steps of:
a) providing a thermally stable porous or fibrous support impregnated with a cyanoacrylate ester and a volatile, emissive lanthanide metal-complex or actinide metal-complex;
b) applying sufficient heat to the support that the cyanoacrylate ester and metal-complex volatilize to form vaporous fumes; and
c) directing the fumes towards a latent fingerprint, whereby, the cyanoacrylate ester and metal-complex fumes co-deposit onto the residual portion of the latent fingerprint to develop the fingerprint.

DETAILED DESCRIPTION OF THE INVENTION

An article of the invention comprises a cartridge containing: 1) a porous or fibrous support impregnated with 2) a cyanoacrylate ester or a polycyanoacrylate ester, and 3) a volatile, emissive lanthanide metal-complex or actinide metal-complex. This is used in a process for developing and visualizing a fingerprint. The cartridge is preferably constructed of a metal such as brass, steel, aluminum, nickel, platinum. The porous or fibrous support can be any thermally resistant material which allows the passage of gases or vapors upon heating. Preferred supports are chemically inert (to the cyanoacrylate and metal complex) fibrous materials such as steel wool or fiberglass. The most preferred supports are steel wool. Any ester of cyanoacrylate or polycyanoacrylate can be used in this invention. Preferred esters of cyanoacrylate are lower alkyl esters (1 to 4 carbon atoms in the alkyl), particularly methyl and ethyl esters.

The volatile, emissive lanthanide or actinide metal-complexes useful in this invention have the following formula:

$$M(\beta\text{-diketonate})_x L_y,$$

where
M is a lanthanide metal ion or an oxo complex of an actinide metal ion;
L is a ligand with a molecular weight not exceeding 150 daltons;
x is an integer ranging from 2 to 4; and
y is an integer ranging from 0 to 3. Preferably, L is water, ammonia, or an ether; y is either 0 or 1; and x is either 2 or 3. Most preferably, x is 3.

As used herein, the term "volatile" refers to a substance which vaporizes or volatilizes without major decomposition (i.e., no more than 50% decomposition) at a temperature between 20° and 300° C.

As also used herein, the term "emissive" refers to a substance which is capable of emitting radiation of a certain wavelength upon excitation by radiation from a light source, the emitted radiation being longer in wavelength than the excitation radiation. Emissiveness includes, for example, fluorescence and phosphorescence.

The metal ions or metal-oxo ions that are useful in this invention are either lanthanide ions (e.g. europium(+3), terbium(+3)) or actinide oxo-ions (e.g. $UO_2^{+2}$). Preferably, the lanthanide or actinide complexes emit light in the visible or infrared portion of the electromagnetic spectrum. Europium complexes, for example, produce an intense orange-red emission when exposed to a proper excitation light (e.g., ultraviolet light). The emissive properties of lanthanide complexes have been described in the literature (see for example, Chapter 25 by L. C. Thompson in *Handbook on the Physics and Chemistry of Rare Earths* edited by K. A. Gschneidner, Jr. and L. Eyring, North-Holland Publishing Company, 1979). Although many lanthanide metal complexes are emissive, europium(+3), terbium(+3), samarium(+3), and dysprosium(+3) are the most emissive. The preferred lanthanide ions are europium(+3) and terbium(+3), while the preferred oxo-actinide ion is uranyl $UO_2^{+2}$.

$\beta$-diketonates are mono-anionic ligands which form very stable metal chelate complexes. They are derived from the corresponding $\beta$-diketones by an enolization and an ionization. (See F. A. Cotton and G. Wilkinson,

*Advanced Inorganic Chemistry*, 5th ed., John Wiley & Sons, New York, 1988, pp 477–479 and references therein for a detailed discussion of β-diketonate ligands). References describing the physical properties, and in some cases the synthesis, of β-diketonate metal complexes are as follows: R. E. Sievers and J. E. Sadlowski, Science, 201, p.217, 1978; C. S. Springer, D. W. Meek, R. E. Sievers, *Inorganic Chemistry*, 6, p.1105, 1967; R. E. Sievers, B. W. Ponder, M. L. Morris, R. W. Moshier, *Inorganic Chemistry*, 4, p.693, 1963; W. R. Wolf, R. E. Sievers, G. H. Brown, *Inorganic Chemistry*, 11, p.1995, 1972; G. M. Kramer, M. B. Dines, R. B. Hall, A. Kaldor, A. J. Jacobson, J. C. Scanlon, *Inorganic Chemistry*, 19, p.1340, 1980. These materials have found use in various applications, e.g. as NMR shift reagents U.S. Pat. No. 3,700,410 describes the preparation and alternative uses for some of these complexes.

β-diketonates useful in the present invention may be generally described by the structure

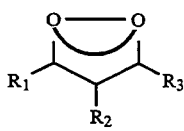

where $R^1$, $R^2$, $R_3$ are independently hydrogen, alkyl, aryl, aralkyl, or alkaryl groups; and $R_2$ and $R_3$ can be connected to form a ring structure.

It is preferred that $R_1$ be a fluoroalkyl group. An especially preferred composition is when $R_1$ is a small fluorocarbon group containing from 1 to 8 carbon atoms and from 1 to 17 fluorine atoms, and $R_2$ is a small, bulky alkyl group such as t-butyl or neopentyl.

In the most common β-diketonate anion, the acetylacetonate anion, $R_1$ and $R_3$ are methyl and $R_2$ is hydrogen. Other typical β-diketonate anions include trifluoroacetylacetonate, hexafluoroacetylacetonate, 2,2,6,6-tetramethyl-3,5-heptanedionate, 6,6,7,7,8,8,8-heptafluoro-2,2-dimethyl-3,5-octanedionate, 1,1,1,5,6,6,7,7,7-decafluoro-2,4-heptanedionate, trifluoroacetyl-d-camphorate, 1,3-diphenyl-1,3-propanedionate, 1-phenyl-1,3-butanedionate, 4,4,4-trifluoro-1-(2-thienyl)-1,3-butanedionate, and 3-(heptafluoropropylhydroxymethylene)-(−)-camphorate.

Following the volatilization of the cyanoacrylate ester and lanthanide or actinide metal-complex, the resultant vaporous fumes of the two compounds selectively co-deposit on any latent fingerprint residue existing on a substrate subjected to the fumes. The cyanoacrylate then polymerizes to expose the fingerprint image. It is believed that the lanthanide or actinide metal-complex catalyzes the polymerization reaction, thereby decreasing the fingerprint cure (and therefore development) time.

Following this process, it is preferred that an excitation light be directed towards the developed fingerprint sample to induce emission by the deposited metal complex. Since the metal complex will have selectively deposited only on the fingerprint residue, such emission serves to enhance the developed fingerprint image. The excitation light may range in wavelength from about 200 to about 600 nm and, preferably, from about 250 to about 450 nm. Any light source capable of producing such wavelengths may be used. Examples of suitable light sources include a high pressure mercury arc lamp, an ultra-high pressure mercury arc lamp, a carbon arc lamp, a xenon arc lamp, a tungsten filament incandescent lamp, a luminescent discharge tube, a cathode ray tube, and various lasers such as argon ion, copper vapor, frequency doubled or tripled Nd:YAG, diode, excimer, and dye lasers.

An advantage of using europium complexes is their intense orange-red emission when the treated fingerprint sample is exposed to UV or blue excitation light. This emission is easily distinguished from other emitting species that might be present on the substrate, such as optical brighteners. In this manner, fingerprint detection is greatly enhanced since the europium complex will have been selectively deposited only on the fingerprint residue.

Fingerprint detection may be further enhanced by using filters to screen out all interfering radiation (e.g., reflectance light, excitation light, unwanted emissions such as from optical brighteners, etc.) so that only emissions from the metal complex deposited on the fingerprint residue are visible. The filters may be selected to match the emission wavelength range of the particular metal complex which is used. In the case of a europium complex, for example, the filters would be selected to allow only the passage of orange-red light.

A surprising observation is that, although the lanthanide and actinide metal-complexes of the present invention have a relatively high molecular weight, such complexes also have a relatively high degree of volatility. Metal complexes having fluorine-containing β-diketonates are especially volatile and are therefore preferred. For example, a europium complex with a fluorinated β-diketonate was observed to have a volatility greater than that of several conventional organic fluorescent compounds having much lower molecular weights. Since volatility is very important for proper deposition on fingerprint residue, the metal complexes of the present invention provide a significant advantage.

A further advantage of the present invention is that the rate of volatilization of lanthanide and actinide metal-complexes is very similar to that of cyanoacrylate esters. The two components thus deposit on the fingerprint sample at approximately the same time so that a substantially homogenous mixture of the two components results on the fingerprint. In this manner, the metal complex will be evenly distributed on the fingerprint residue so that, when emission is induced from the metal complex, the emissive image emanates from substantially all portions of the fingerprint.

The preparation of the cartridge can be accomplished by a number of methods. The important feature is that the cyanoacrylate and the metal complex are placed on the inert substrate in close enough proximity such that, upon heating, the two materials effectively co-volatilize. For example, the cyanoacrylate and metal complex may be added sequentially to the substrate, by first adding a cyanoacrylate ester, then a curing agent, and finally a metal complex solution.

In order that the invention may be more readily understood, reference is made to the following examples, which are intended to be illustrative of the invention, but are not intended to be limiting in scope.

EXAMPLES

Materials. Sievers' Reagent (tris(6,6,7,7,8,8,8-heptafluoro-2,2-dimethyl-3,5-octanedionato)europium) was obtained from Aldrich Chemical Company and was listed as Resolve-Al EuFOD ™ (cat. no. 16,093-8).

Loctite Hard Evidence, obtained from Lightning Powder Co., Inc., 1230 Hoyt St., S. E., Salem, Oreg. 97302, was the cyanoacrylate employed. Zip-Kicker, is a cyanoacrylate curing agent, available from Pacer, Rancho Cucamonga, Calif. 91730. All other materials were obtained from standard sources. The aminostyryl derivatives, 4-diethylaminobenzalmalononitrile and 4-tricyanovinyl-N,N-diethylaniline, used in the comparative thermogravimetric analysis example were and can be prepared by the methods listed in B. C. Mckusick, et. al. *J. Am. Chem. Soc.* 80,1958, 2806. The other compound used in the thermogravimetric analysis study, 2-(o-hydroxyphenyl)-benzothiazole, was obtained from Eastman Fine Chemicals.

Equipment. A model UT-1005Si butane powered heat tool from Master Appliance Corporation, 2420 18th St., Racine, Wis. 53401 was used as the heating source. The UV source was a Model UVG-11 Mineralight Lamp (Short Wavelength UV-254 nm) handheld unit from UVP. Inc., San Gabriel, Calif.

Preparation of Cartridges

A dichloromethane solution, ~5% by weight of Sievers' reagent was prepared. A brass cartridge, prepared by modifying a 0.22–250 shell casing, was packed with steel wool. This cartridge was packed with the steel wool such that the steel wool formed a torus in the cartridge; this design allows the hot vapors to escape through the central channel. The steel wool was impregnated with the cyanoacrylate (Loctite) and sprayed with the curing agent (Zip-Kicker). A few drops of the metal complex-containing solution was added to the cyanoacrylate impregnated steel wool and the solvent was allowed to evaporate.

Development of Fingerprints

The butane heater was started and when the ceramic element started to glow red, the cartridge was placed on the top of the burner. Within seconds, fumes began to develop. The fumes were allowed to come in contact with a glass slide which had been touched so as to provide a fingerprint. Within seconds an enhanced fingerprint was observed. Irradiation of the enhanced image with the UV light resulted in a orange-red emission from the fingerprinted region.

Volatility Analysis

The relative volatility of several fluorescent organic compounds was compared to that of Sievers' reagent (europium metal complex) and cyanoacrylate by thermogravimetric analysis using a Perkin-Elmer 7 Series Thermal Analysis System. While air was caused to flow over each sample at 50 cc/min, the samples were heated from room temperature to 300° C. at 40° C./min, and then held at 300° C. for 10 min. The results are shown in Table 1. The volatility of the metal complex exceeds that of the organic compounds, despite having a molecular weight approximately three to four times greater. In addition, the rate of volatility of the europium metal complex was closer to that of the cyanoacrylate than any of the fluorescent organic compounds tested.

TABLE 1

| TIME TO 50% WEIGHT LOSS* | |
|---|---|
| COMPOUND | MINUTES |
| Cyanoacrylate | 4.0 |
| Europium Metal Complex | 5.9 |
| o-hydroxyphenyl benzothiazole | 6.4 |
| 4-diethylaminobenzalmalononitrile | 7.3 |
| Tricyanovinyl N,N-diethylaniline | 8.3 |

*At Time = 0, Temperature = 20° C., Heating Rate of 40° C./minute for 7 minutes. Isothermal at 300° C. for 10 minutes. Airflow - 50 cc/minutes.

What is claimed is:

1. A cartridge comprising a housing with a chamber therein and an outlet from said chamber, said chamber containing a thermally stable porous or fibrous support impregnated with both:
   a) a cyanoacrylate ester, and
   b) a volatile, emissive lanthanide or actinide metal-complex having β-diketone ligands.

2. The cartridge of claim 1, wherein said porous or fibrous support is steel wool or glass wool.

3. The cartridge of claim 1, wherein said cyanoacrylate ester is a polycyanoacrylate ester comprising polymethylcyanoacrylate or polyethylcyanoacrylate.

4. The cartridge of claim 1, wherein said volatile, emissive lanthanide or actinide metal-complex has the formula

$$M(\beta\text{-diketonate})_x L_y,$$

where
M is a lanthanide metal ion or an oxo complex of an actinide metal ion;
L is a ligand with a molecular weight not exceeding 150 daltons;
x is an integer ranging from 2 to 4; and
y is an integer ranging from 0 to 3.

5. The cartridge of claim 4, wherein M comprises europium(+3) or terbium(+3).

6. The cartridge of claim 4, wherein M comprises $UO_2^{+2}$.

7. The cartridge of claim 4, wherein said β-diketonate has the structure:

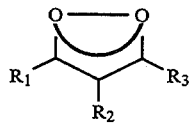

where
$R_1$, $R_2$, $R_3$ are independently alkyl, aryl, aralkyl, or alkaryl groups; a fluorine-containing alkyl or aryl group having from 1–8 carbon atoms and from 3–17 fluorine atoms; or hydrogen, and
$R_2$ and $R_3$ can be connected to form a ring structure.

8. The cartridge of claim 4, wherein said β-diketonate is selected from the group consisting of acetylacetonate, trifluoroacetylacetonate, hexafluoroacetylacetonate, 2,2,6,6-tetramethyl-3,5-heptanedionate, 6,6,7,7,8,8,8-heptafluoro-2,2-dimethyl-3,5-octanedionate, 1,1,1,5,6,6,7,7,7-decafluoro-2,4-heptanedionate, trifluoroacetyl-d-camphorate, 1,3-diphenyl-1,3-propanedionate, 1-phenyl-1,3-butanedionate, 4,4,4-trifluoro-1-(2-thienyl)-1,3-butanedionate, and 3-(heptafluoropropylhydroxymethylene)-(−)-camphorate.

9. The cartridge of claim 8, wherein said β-diketonate is 6,6,7,7,8,8,8-heptafluoro-2,2-dimethyl-3,5-octanedionate.

10. The cartridge of claim 1 wherein said volatile, emissive lanthanide or actinide metal-complex contains the fragment M(β-diketonate), where
M is a lanthanide metal ion comprising europium(+3) or terbium(+3); and
the β-diketonate has the structure:

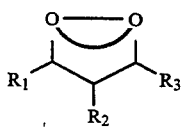

where $R_1$, $R_2$, $R_3$ are independently alkyl, aryl, aralkyl, or alkaryl groups; a fluorine-containing alkyl or aryl group having from 1–8 carbon atoms and from 3–17 fluorine atoms; or hydrogen, and $R_2$ and $R_3$ can be connected to form a ring structure.

11. The cartridge of claim 1 wherein said volatile, emissive lanthanide or actinide metal-complex contains the fragment M(β-diketonate), where
M is a lanthanide metal ion comprising europium(+3) or terbium(+3); and
the β-diketonate is selected from the group consisting of acetylacetonate, trifluoroacetylacetonate, hexafluoroacetylacetonate, 2,2,6,6-tetramethyl-3,5-heptanedionate, 6,6,7,7,8,8,8-heptafluoro-2,2-dimethyl-3,5-octanedionate, 1,1,1,5,6,6,7,7,7-decafluoro-2,4-heptanedionate, trifluoroacetyl-d-camphorate, 1,3-diphenyl-1,3-propanedionate, 1-phenyl-1,3-butanedionate, 4,4,4-trifluoro-1-(2-thienyl)-1,3-butanedionate, and 3-(heptafluoropropylhydroxymethylene)-(−)-camphorate.

12. A fingerprint development composition comprising a monomeric or polymeric cyanoacrylate and a volatile, emissive lanthanide or actinide metal-complex having the formula $M(\beta\text{-diketonate})_x L_y$, where
M is a lanthanide metal ion or an oxo complex of an actinide metal ion;
L is a ligand with a molecular weight not exceeding 150 daltons;
x is an integer ranging from 2 to 4; and
y is an integer ranging from 0 to 3.

13. The composition of claim 12, wherein M comprises europium(+3) or terbium(+3).

14. The composition of claim 12, wherein M comprises $U_2{}^{+2}$.

15. The composition of claim 12, wherein said β-diketonate has the structure:

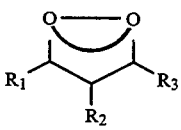

where $R_1$, $R_2$, $R_3$ are independently alkyl, aryl, aralkyl, or alkaryl groups; a fluorine-containing alkyl or aryl group having from 1–8 carbon atoms and from 3–17 fluorine atoms; or hydrogen, and
$R_2$ and $R_3$ can be connected to form a ring structure.

16. The composition of claim 12, wherein said β-diketonate is selected from the group consisting of acetylacetonate, trifluoroacetylacetonate, hexafluoroacetylacetonate, 2,2,6,6-tetramethyl-3,5-heptanedionate, 6,6,7,7,8,8,8-heptafluoro-2,2-dimethyl-3,5-octanedionate, 1,1,1,5,6,6,7,7,7-decafluoro-2,4-heptanedionate, trifluoroacetyl-d-camphorate, 1,3-diphenyl-1,3-propanedionate, 1-phenyl-1,3-butanedionate, 4,4,4-trifluoro-1-(2-thienyl)-1,3-butanedionate, and 3-(heptafluoropropylhydroxymethylene)-(−)-camphorate.

17. The composition of claim 16, wherein said β-diketonate is 6,6,7,7,8,8,8-heptafluoro-2,2-dimethyl-3,5-octanedionate.

18. A method for developing a latent fingerprint, comprising the steps of:
a) providing a thermally stable porous or fibrous support impregnated with a cyanoacrylate ester and a volatile, emissive lanthanide or actinide metal-complex having β-diketone ligands;
b) applying sufficient heat to said support that said cyanoacrylate ester and said metal-complex volatilize to form vaporous fumes; and
c) directing said fumes towards a latent fingerprint, whereby, said cyanoacrylate ester and said metal-complex fumes co-deposit onto the residual portion of said latent fingerprint to develop said fingerprint.

19. The method of claim 18, further including the step of directing excitation light towards said developed fingerprint, thereby inducing emission by said deposited metal-complex to enhance the visualization of said developed fingerprint.

20. The method of claim 18, wherein said porous or fibrous support is steel wool or glass wool.

21. The method of claim 18, wherein said cyanoacrylate ester is a polycyanoacrylate ester comprising polymethylcyanoacrylate or polyethylcyanoacrylate.

22. The method of claim 18, wherein said volatile, emissive lanthanide or actinide metal-complex has the formula $M(\beta\text{-diketonate})_x L_y$, where
M is a lanthanide metal ion or an oxo complex of an actinide metal ion;
L is a ligand with a molecular weight not exceeding 150 daltons;
x is an integer ranging from 2 to 4; and
y is an integer ranging from 0 to 3.

23. The method of claim 22, wherein M comprises europium(+3) or terbium(+3).

24. The method of claim 22, wherein M comprises $UO_2{}^{+2}$.

25. The method of claim 22, wherein said β-diketonate has the structure:

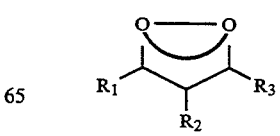

where $R_1$, $R_2$, $R_3$ are independently alkyl, aryl, aralkyl, or alkaryl groups; a fluorine-containing alkyl or aryl group having from 1-8 carbon atoms and from 3-17 fluorine atoms; or hydrogen, and $R_2$ and $R_3$ can be connected to form a ring structure.

26. The method of claim 22, wherein said β-diketonate is selected from the group consisting of acetylacetonate, trifluoroacetylacetonate, hexafluoroacetylacetonate, 2,2,6,6-tetramethyl-3,5-heptanedionate, 6,6,7,7,8,8,8-heptafluoro-2,2-dimethyl-3,5-octanedionate, 1,1,1,5,6,6,7,7,7-decafluoro-2,4-heptanedionate, trifluoroacetyl-d-camphorate, 1,3-diphenyl-1,3-propanedionate, 1-phenyl-1,3-butanedionate, 4,4,4-trifluoro-1-(2-thienyl)-1,3-butanedionate, and 3-(heptafluoropropylhydroxymethylene)-(−)-camphorate.

27. The method of claim 26, wherein said β-diketonate is 6,6,7,7,8,8,8-heptafluoro-2,2-dimethyl-3,5-octanedionate.

28. The method of claim 18 wherein said volatile, emissive lanthanide or actinide metal-complex contains the fragment M(β-diketonate), where M is a lanthanide metal ion comprising europium(+3) or terbium(+3); and
the β-diketonate has the structure:

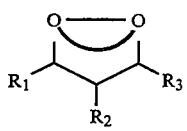

where $R_1$, $R_2$, $R_3$ are independently alkyl, aryl, aralkyl, or alkaryl groups; a fluorine-containing alkyl or aryl group having from 1-8 carbon atoms and from 3-17 fluorine atoms; or hydrogen, and $R_2$ and $R_3$ can be connected to form a ring structure.

29. The method of claim 18 wherein said volatile, emissive lanthanide or actinide metal-complex contains the fragment M(β-diketonate), where M is a lanthanide metal ion comprising europium(+3) or terbium(+3); and
the β-diketonate is selected from the group consisting of acetylacetonate, trifluoroacetylacetonate, hexafluoroacetylacetonate, 2,2,6,6-tetramethyl-3,5-heptanedionate, 6,6,7,7,8,8,8-heptafluoro-2,2-dimethyl-3,5-octanedionate, 1,1,1,5,6,6,7,7,7-decafluoro-2,4-heptanedionate, trifluoroacetyl-d-camphorate, 1,3-diphenyl-1,3-propanedionate, 1-phenyl-1,3-butanedionate, 4,4,4-trifluoro-1-(2-thienyl)-1,3-butanedionate, and 3-(heptafluoropropylhydroxymethylene)-(−)-camphorate.

* * * * *

UNITED STATES PATENT AND TRADEMARK OFFICE
CERTIFICATE OF CORRECTION

PATENT NO. : 5,342,645
DATED : August 30, 1994
INVENTOR(S) : John F. Eisele, Terrance P. Smith, and Michael C. Palazzotto It is certified that error appears in the above-indentified patent and that said Letters Patent is hereby corrected as shown below:

The β-diketonate structure is wrong throughout the patent. The bond between the two oxygens at the top of the structure should be a "negative" sign, appearing lower than the two oxygens, and the semi-circle should be lower; the structure should appear as follows:

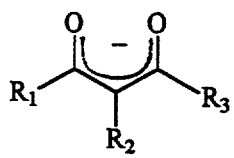

COLUMN 8, LINE 16 AND COLUMN 10, LINE 24:
In Claims 1 and 18, the words "β-diketone" should be --β-diketonate--.

In Claims 1 and 18, before the words "β-diketonate", add the words --one or more--.
COLUMN 9, LINE 58:
In Claims 14, the words "$U_2^{+2}$" should be --$UO_2^{+2}$--.

Signed and Sealed this

Twenty-eight Day of February, 1995

Attest:

BRUCE LEHMAN

Attesting Officer   Commissioner of Patents and Trademarks